United States Patent
Moulis et al.

(10) Patent No.: US 9,836,834 B2
(45) Date of Patent: Dec. 5, 2017

(54) TOPOLOGY-PRESERVING ROI REMAPPING METHOD BETWEEN MEDICAL IMAGES

(71) Applicant: INTRASENSE, Montpellier (FR)

(72) Inventors: Marc Moulis, Gigean (FR); Charles Caderas De Kerleau, Carnon (FR)

(73) Assignee: INTRASENSE, Montpellier (FR)

( * ) Notice: Subject to any disclaimer, the term of this patent is extended or adjusted under 35 U.S.C. 154(b) by 95 days.

(21) Appl. No.: 14/390,237

(22) PCT Filed: Mar. 27, 2013

(86) PCT No.: PCT/EP2013/056608
§ 371 (c)(1),
(2) Date: Oct. 2, 2014

(87) PCT Pub. No.: WO2013/149920
PCT Pub. Date: Oct. 10, 2013

(65) Prior Publication Data
US 2015/0049932 A1    Feb. 19, 2015

(30) Foreign Application Priority Data
Apr. 3, 2012   (EP) .................................... 12305397

(51) Int. Cl.
*G06T 7/00*    (2017.01)
*G06T 7/30*    (2017.01)
*G06T 7/33*    (2017.01)
*A61B 6/00*    (2006.01)

(52) U.S. Cl.
CPC .......... *G06T 7/0012* (2013.01); *A61B 6/5235* (2013.01); *G06T 7/30* (2017.01); *G06T 7/337* (2017.01); *A61B 6/469* (2013.01); *G06T 2207/10081* (2013.01);
(Continued)

(58) Field of Classification Search
None
See application file for complete search history.

(56) References Cited

U.S. PATENT DOCUMENTS 7,689,021 B2 *   3/2010  Shekhar ............... G06K 9/6207
                                              382/128
7,817,835 B2    10/2010  Fan et al.
(Continued)

OTHER PUBLICATIONS

Goldwasser et al., "Techniques for the Rapid Display and Manipulation of 3-D Biomedical Data," Computerized Medical Imaging and Graphics (1988), 12(1), pp. 1-24.

*Primary Examiner* — Bernard Krasnic
(74) *Attorney, Agent, or Firm* — Greer, Burns & Crain, Ltd.

(57) ABSTRACT

A method is provided for calculating a region of interest in a second image using an initial region of interest in a first image. The first and second images are linked by a spatial transformation function. The method includes steps of (i) generating a first polygonal mesh enclosing the initial region of interest in the first image; (ii) computing a second polygonal mesh in the second image by applying the spatial transformation function to the first polygonal mesh, and (iii) identifying image elements within the second image, that belong to the area enclosed by the second polygonal mesh. Also provided are a computer program and a system.

11 Claims, 2 Drawing Sheets

(52) U.S. Cl.
CPC .............. *G06T 2207/10088* (2013.01); *G06T 2207/10104* (2013.01); *G06T 2207/10136* (2013.01)

(56) References Cited

U.S. PATENT DOCUMENTS

| | | | |
|---|---|---|---|
| 2008/0007559 A1* | 1/2008 | Kalaiah | H04N 13/0275 345/501 |
| 2010/0027861 A1* | 2/2010 | Shekhar | G06K 9/6207 382/131 |
| 2010/0286517 A1 | 11/2010 | Kamen et al. | |
| 2011/0178389 A1 | 7/2011 | Kumar et al. | |

* cited by examiner (a)

(b)

(c)

(d)

(e)

(f)

(g)

(h)

(i)

(j)

TOPOLOGY-PRESERVING ROI REMAPPING METHOD BETWEEN MEDICAL IMAGES

BACKGROUND

The invention relates to a topology-preserving transposition method for transposing a Region of Interest (ROI) from a source image to a destination image.

The field of the invention is the processing and analysis of medical images.

Regions of Interest, or ROI, are used to isolate or extract areas of interest in medical images, in order to perform measurements or any other tasks on these areas.

Medical images include for instance images issued from Computed Tomography (CT), Magnetic Resonance Imaging (MRI), Positron Emission Tomography (PET), or medical ultrasonography.

Medical images are usually represented as collections of picture elements, such as pixels for the bi-dimensional (2D) images or voxels for the tree-dimensional (3D) or volume images.

ROI can be represented as a collections of picture elements identified or labelled as belonging to, for instance, an anatomical structure (lung, blood vessel, . . . ) or a pathological structure (nodules, . . . ). ROI can be created manually, by an operator who identifies the picture elements corresponding to a specific structure and tags them. They can also be created by means of automated or semi automated methods using picture analysis tools and a-priori knowledge.

During clinical exams, it is often desirable to transfer a ROI from one image or one series of images to another, for instance for a longitudinal follow-up of a patient, or for comparison or cross measurement purposes.

The images may be acquired with the same modality or imaging technique at different times, or using different acquisition channel.

They may also be acquired with different modalities which allow for instance accessing to different types of information. For instance, a CT technique may be used to obtain images with structural or anatomical information, and PET technique may be used to obtain functional information on the same anatomical structures.

In general, it is not desirable, or even not possible to re-compute a ROI independently in each of the image series: It would be too time consuming, and there would be a risk that the segmentation process does not lead to a ROI corresponding to exactly the same anatomical structure. Furthermore, sometimes a ROI may be computed in an image series (for instance a structural one) but the anatomical structure may not be recognizable in another image series (for instance a functional one) or distinct enough for segmentation and so the ROI may not be computed in the latter image series.

A solution is to transpose a ROI computed in one image series to another image series. But several problems may appear: the spatial sampling of the images may be different, and there may be deformations of the imaged anatomical structures between the image series. The deformations may be of the rigid type (translations, rotations, scaling) and/or of the soft type (deformations of the anatomical structures into the images). They may be due for instance to differences in image modalities, imaging positions, and/or motions of the patient or of the anatomical structures themselves (breathing . . .).

Soft or rigid deformations between images are usually taken into account during radiological exams through a registration process. Transfer functions corresponding to soft and/or rigid deformations between images are computed, on the basis of manual and/or automated identifications of corresponding structures in the images. But in particular in the case of soft registration (i.e. taking into account soft deformations), these transfer function do not result in the general case to a pixel-to-pixel correspondence between images.

We know for instance the document U.S. Pat. No. 7,817,835 which describes a method for doing cross reference measurements between images. Measurements done in a source image and represented or materialized by mark locations such as segments, circles . . . drawn in that source image, are transposed to a destination image using registration information. Then the same measurements are done independently in the destination image and compared to the transposed measurements.

However, the method is not applicable to ROI transposition because in the general case, a point-by-point transposition of an area in a source image does not lead to a coherent representation of a corresponding area in a destination image. And in addition, the method of U.S. Pat. No. 7,817,835 is limited to rigid registration.

It is an object of the invention to provide a method for transposing a ROI from a source image to a destination image using soft and/or rigid image registration information.

It is a further object of the invention to provide a method for transposing a ROI from a source image to a destination image which allows optimizing the calculation requirements.

It is a further object of the invention to provide a method for defining a ROI in a destination image in which it cannot be easily obtained, using a ROI obtained in a source image.

It is a further object of the invention to provide a method for defining a ROI in a destination image using a segmented reference image.

SUMMARY

Such objects are accomplished through a method for calculating a region of interest in a second image using an initial region of interest in a first image, said first and second images being linked by a spatial transformation function, characterized in that it comprises steps of:
  generating a first polygonal mesh enclosing said initial region of interest in the first image,
  computing a second polygonal mesh in said second image by applying said spatial transformation function to said first polygonal mesh,
  identifying image elements within said second image, that belong to the area enclosed by said second polygonal mesh.

According to some modes of realization, the spatial transformation function may comprise soft deformations.

The spatial transformation function may in particular comprise elastic or plastic deformations.

The first and second images may comprise bi-dimensional (2D) images whose picture elements are pixels.

According to some preferred modes of realization, the first and second images may comprise tri-dimensional (3D) images, whose picture elements are voxels.

The method of the invention may further comprise the steps of:
  decomposing a 3D second image as a stack of 2D second images,
  computing 2D regions of interest in said 2D second images, and combining said 2D regions of interest to obtain a 3D region of interest.

The method of the invention may further comprise the steps of:
  computing intersections of the second polygonal mesh with a 2D second image, so as to generate a 2D contour image, and
  identifying image elements of said 2D second image, that belong to the area(s) enclosed by contours of the 2D contour image.

The method of the invention may further comprise the steps of:
  generating an octree storing references to the locations of the second polygonal mesh's faces, and
  computing intersections of said second polygonal mesh with said 2D second image using said octree, to limit said computing to relevant faces, or to second polygonal mesh's faces located in said 2D second image's area.

An octree is a well-known tree data structure in which each internal node has eight children. It allows partitioning the 3D space by recursively subdividing it into eight octants, so as to allow a very efficient and fast spatial indexing.

The method of the invention may further comprise the steps of:
  applying to the 2D contour image a connected components detection, so as to obtain a 2D image where 2D areas located outside any closed shape are marked as "outside",
  creating a depth map image in the form of a buffer associating to the pixels of said 2D image one of the following depth values: the complimentary values "inside" or "outside", or "undefined",
  initializing in said depth map the pixels previously identified as "outside" by the connected components detection to "outside" value,
  filling said depth map by iteratively identifying areas enclosed by contours from the outermost to the innermost contour, each contour separating "outside" pixels and "inside" pixels, said "inside" pixels defining the 2D regions of interest.

The method of the invention may further comprise the steps of initializing a current depth value to "outside", and repeating iteratively, for all contours in the 2D contour image, the steps of:
  extracting an outermost contour's exterior hull in said 2D contour image using a contour following algorithm, said outermost contour being chosen from a criterion related to its vicinity with the borders of the image,
  applying connected components detection on said contour hull so as to generate distinct areas corresponding to, respectively: the outside of the contour, the contour and the interior of the contour,
  updating the depth map by marking hull contour pixels with current depth value, and hull's interior area pixels with current depth's complementary value,
  removing said extracted contour from said 2D contour image, and
  setting the current depth value to its complementary value for the next iteration.

According to some modes of realization, the spatial transformation function may comprise only rigid body transformations and/or scaling.

The rigid body transformations may comprise for instance translations and rotations.

The method of the invention may further comprise the steps of:
  generating a first polygonal mesh enclosing the initial region of interest in the first image,
  identifying couples of first picture elements of said first polygonal mesh, that bound line segments included in said initial region of interest and oriented along at least one direction of said first image,
  computing a second polygonal mesh in the second image by applying the spatial transformation function to said couples of first picture elements, so as to compute corresponding couples of second picture elements,
  computing picture elements of said second image, that belong to line segments bounded by said corresponding couples of second picture elements, using a rasterization algorithm and taking into account a segment thickness so as to avoid any space left between neighboring segments.

According to some modes of realization,
  the spatial samplings for the first and second images may be different;
  the first image may be a reference image or an image from an anatomical atlas;
  the first and second images may be acquired using distinct medical imaging techniques, or different modalities, or different acquisition channels;
  the first and second images may be acquired using at least one of the following medical imaging techniques: computed tomography (CT), magnetic resonance imaging (MRI), positron emission tomography (PET), ultrasound imaging.

According to another aspect, it is proposed a computer program comprising instructions for carrying out the steps of the method of the invention, when said computer program is executed on a computer system.

According to still another aspect, it is proposed an image processing system comprising means adapted to carry on the steps of the method of the invention.

So, the method of the invention allows transposing a Region of Interest (ROI) from a first or source image to a second or destination image using a topology-preserving transposition process. This process takes into account any type of registration pre-processing (rigid or soft) that may have been performed between the source and destination images.

The method of the invention may for instance be used to transpose a ROI enclosing a detected pathology from a source 3D image, where the pathology is visible, to a destination 3D image where the pathology is not visible or has a fuzzy or undetermined boundary, in order to perform specific or additional measurements for the characterization of this pathology. For instance, the source image may be an anatomical CT image, and the destination image may be a functional PET image.

The ROI may also be an anatomical structure which may be segmented in the first or source image, and transposed to the destination image where a direct segmentation of the same structure would be less efficient or more time-consuming, or even impossible.

The method of the invention may also be used to transpose or map a ROI derived from a theoretical or generic anatomical model to an image from a patient.

For instance, the method of the invention may be used to project an atlas from a labeled "reference" CT image to a destination anatomical CT image while compensating variability between the reference and the destination images.

The initial ROI may be also derived from a first patient, and transposed to an image from a second patient.

The method of the invention may also be used to initiate a new segmentation in the destination image by using the transposed ROI as a "first guess", for instance:

during a breathing cycle, to segment lungs in a destination 3D image on the basis of a first estimate coming from a source 3D image, during a longitudinal follow-up, to segment a lung nodule in a series acquired at times T1 from a previous series acquired at earlier times T0 where the nodule was already segmented.

The method of the invention may also be used for doing a resolution remapping of a ROI. The method may then allow computing an over-sampled version of a ROI by transposing a ROI from an image with a coarse sample grid to an image with a finer one, so as to allow performing more precise measurements on the refined ROI.

As already explained, projecting a set of voxels defining a consistent 3D shape (or pixels for 2D images) from one space to another through a mathematical function induces many problems, the major one being that projected voxels may be scattered in the destination space thus inducing the loss of topological properties.

It is an advantage of the method of the invention to solve this issue by (i) transforming the discrete set of voxels defined in the discrete source space (the source 3D image) into a simplex-based representation (e.g. triangles or quadrangles, etc.), (ii) projecting only some defined vertices of such representation in the destination discrete space (the destination 3D image), and then (iii) re-discretizing the projected simplex-based shape in this destination discrete space as a consistent set of voxels.

It is also an advantage of the method to use technical approaches specifically adapted to the medical imaging context, such as processing 3D images as stacks of 2D images, which is the way in which several medical imaging techniques such as MRI acquire the images.

It is a further advantage of the method to allow linking the sets of voxels of the source and destination ROI in order to perform any cross-modality analysis and measurement without undue simplification or loss of information.

BRIEF DESCRIPTION OF THE DRAWINGS

The methods according to embodiments of the present invention may be better understood with reference to the drawings, which are given for illustrative purposes only and are not meant to be limiting. Other aspects, goals and advantages of the invention shall be apparent from the descriptions given hereunder.

DETAILED DESCRIPTION

Figure 1:
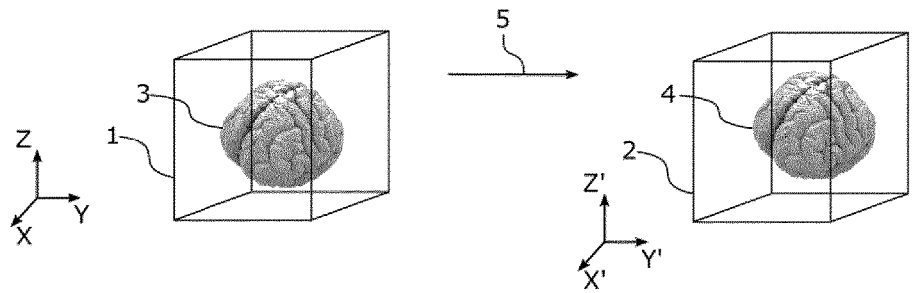
FIG. 1 illustrates the method of the invention applied to 3D images.
Figure 2:
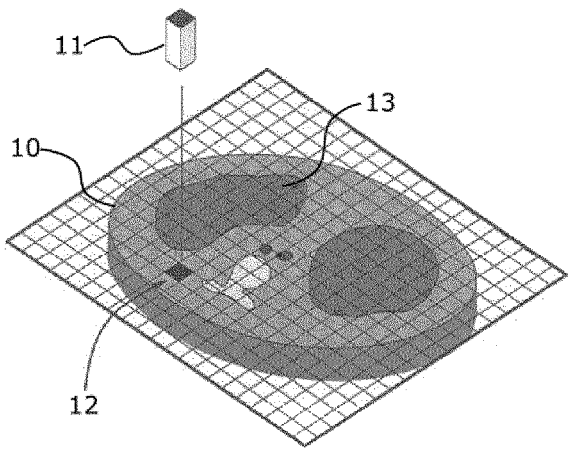
FIG. 2 illustrates a 2D slice image, with 2D ROI.

With reference to FIG. 1, the method of the invention allows calculating a region of interest (ROI) 4 in a second or a destination image 2 using an initial region of interest (ROI) 3 in a first or a source image 1. With reference to FIG. 2, the source and destination images may be 3D images composed of 3D picture elements, or voxels 11. The 3D images may usually be represented as stacks of 2D images 10 composed of 2D picture elements, or pixels 12.

A region of interest (ROI) of a 3D image 3 is an area of the image whose voxels 11 have been labeled as belonging to a specific structure, for instance during a segmentation process. In the example of FIG. 1, only a ROI 3 corresponding to a brain is shown.

If the 3D image is represented as a stack of 2D images or 2D slices, the 3D ROI appears in the 2D images 10 as a collection of labeled pixels 12 forming a 2D ROI 13.

In order to be able to compare and use the images together, the source image 1 and the destination image 2 must be linked during a registration process. This process is common in medical imaging, so it is not described in detail here.

The registration process consists in computing a spatial transformation function 5 which describes the spatial deformations between a source image 1 and a destination image 2. These deformations may be due to differences in the imaging modalities or techniques, and/or movements of the patient, for instance.

The spatial transformation function 5 allows establishing a relation between picture elements of source image 1 and of the destination image 2, so as to be able to correct the deformations of one image relative to the other and allow a good matching of the images. It may be computed in the form of a function or a correspondence table between the images.

A spatial transformation function 5 may be computed using the following method:

identifying (manually and/or automatically) remarkable anatomical features which can be found in both images;

selecting a deformation model;

if a rigid deformation model is used, comprising translations, rotations and/or scaling of the whole image, computing the best fit parameters of the model so as to be able to superpose as much as possible the remarkable anatomical features of both images;

if a soft deformation model is used, superposing the locations of the remarkable anatomical features of the images and computing the local deformations between these features on the basis of a physical deformation model (for instance an elastic deformation model) or a mathematical deformation model (by mathematical interpolation, . . . ).

First Mode: Rigid Registration

Figure 3:
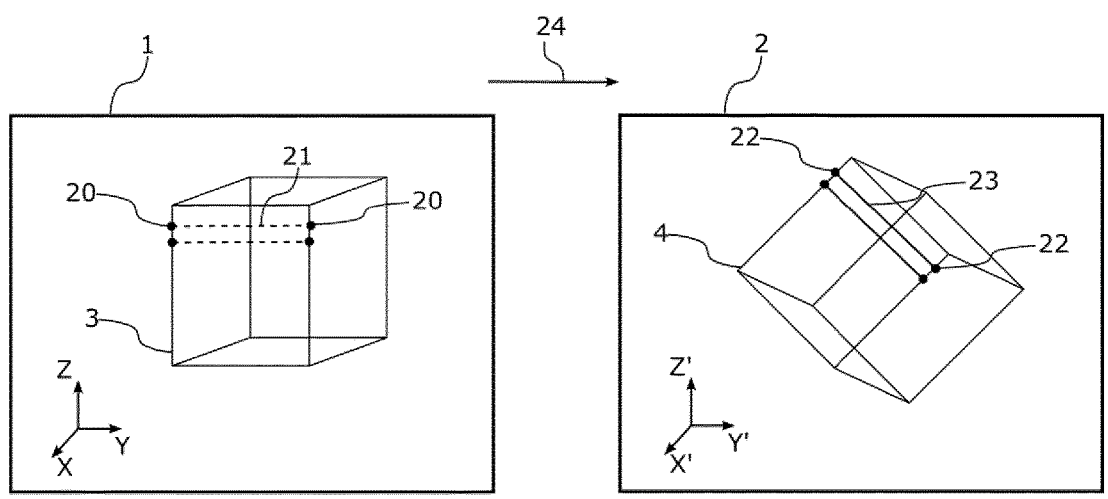
FIG. 3 illustrates the method of the invention when only rigid registration is considered.

With reference to FIG. 3, we will describe a first mode of implementation of the method of the invention, which is applicable when only rigid registration is used. In that case, the spatial transformation function 24 between the source image 1 and the destination image 2 may comprise only translations, rotations and/or scaling.

This mode of implementation, when applicable, allows achieving shorter computation time. It comprises the following steps:

1) computing the contour of the source ROI 3 by generating a polygonal mesh that approximates the ROI's surface;

2) in the source image 1, identifying the couples of points 20 which belong to the contour of the ROI 3 and which are on the same line segment 21 along a direction of the sampling grid (for instance the X axis);

3) applying the spatial transformation function 24 to these couples of points 20 to compute the corresponding couples of points 22 in the destination image 2;

4) using a rasterization algorithm such as the Bresehnam algorithm, computing the voxels which belong to the line segment 23 between the couple of points 22 of the destination image 2. To take into account the differences in scaling and/or sampling between the source and the destination images, applying a thickness parameter to the line segments 23 so that no voxel is left between adjacent line segments 23.

The destination or transposed ROI 4 is then composed of the voxels which have been identified during the rasterization process.

This method is applicable as long as the spatial transformation function 24 is such as the transposed line segments 23 in the destination image 2 remain parallel to each others.

Of course, the same process may be repeated along other directions of the sampling grid of the source image (for instance the Y or Z axis).

Second Mode: Rigid and Soft Registration

Figure 4:
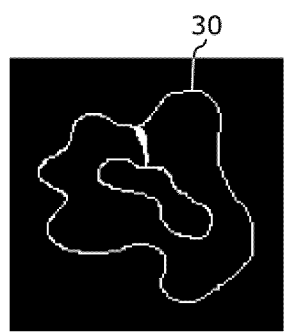
FIGS. 4a to FIG. 4j illustrate the steps of the method when soft or rigid registrations are considered.
Figure 4:
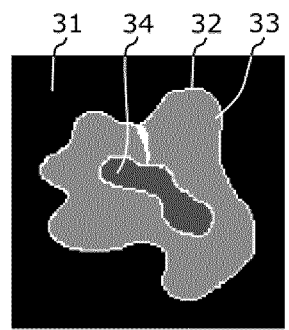
Figure 4:
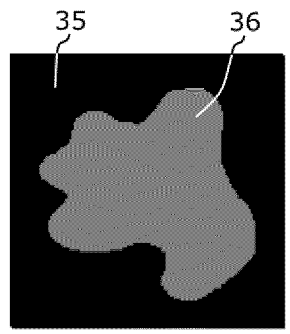
Figure 4:
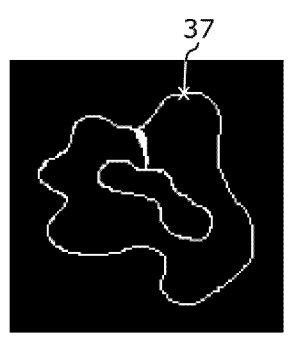
Figure 4:
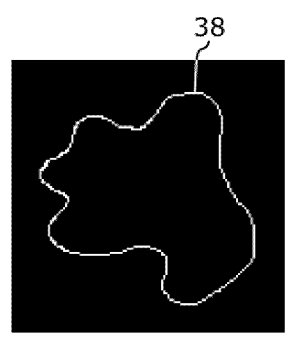
Figure 4:
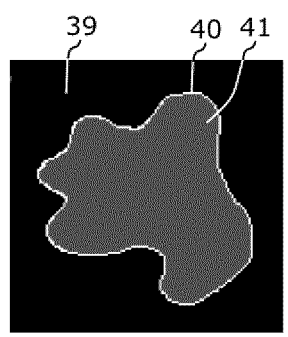
Figure 4:
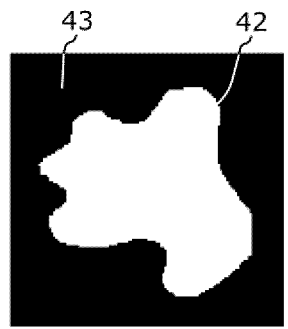
Figure 4:
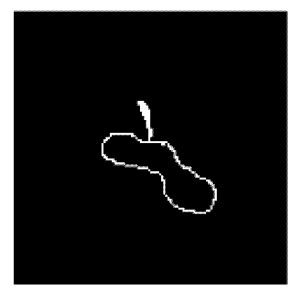
Figure 4:
Figure 4:
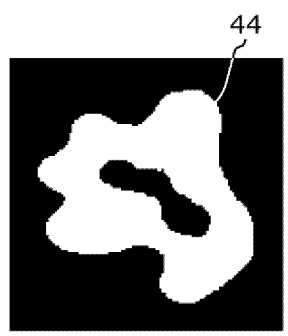

With reference to FIG. 4, we will describe a second mode of implementation of the method of the invention, which is applicable with any kind of rigid and/or soft registration.

It comprises the following steps:

1) computing the contour of the source ROI 3 in the source image 1 by generating a polygonal mesh that approximates the ROI's surface;

2) deforming the polygonal mesh using the spatial transformation function 5, to compute the corresponding deformed mesh into the destination image 2 space;

3) generating an octree that stores references to the deformed mesh's faces.

4) processing the destination image 2 slice by slice. It is important to remark that medical images are already usually stored as stacks of 2D slices, and that they are also frequently acquired in that way (as MRI for instance);

5) computing the intersection of the destination volume's slices with the deformed polygonal mesh using the octree to limit the operation to relevant faces, and generating a 2D contour image (FIG. 4a) that represents these intersections 30. Each destination slice is tested against the octree to determine the sub-set of triangles that might intersect the slice's plane. The 2D contour images are then the result of the intersection 30 of the deformed polygonal mesh's triangles with the planes supporting the slices of the destination volume. For each intersecting triangle, the shape of the intersection 30 with the supporting plane is drawn in 2D in the image representing the current slice. The intersection 30 of a triangle with a non-thick plane is either empty, either a single pixel, either a line, or the triangle itself if it is contained in the plane;

6) filling the contour image using a 2D filling process which is described below, so as to identify the pixels of the slice belonging to the 2D slice of the destination ROI 4 (FIG. 4j);

7) combining the filled 2D contours images to build the destination ROI 4.

The 2D filling process allows relatively fast processing while ensuring correct results in the vast majority of cases. The basic idea is to "peel out" successive layers (or groups) of pixels of the 2D image slice, based on their connectivity with "outside pixels", so that these layers or groups can be identified as "inside" or "outside".

The 2D filling process comprises the following steps:

1) taking a "contour image" (FIG. 4a) as an input, and applying a connected components detection algorithm. Connected components detection, or blob detection, refers to a class of well known algorithms which allows identifying groups of pixels 12 which share some properties with their neighbors, in order to segment the pixels in groups based on these properties. The result here is a 2D image (FIG. 4b) where all 2D areas 31 located outside any closed shape are marked as "outside". More precisely, on the example of FIG. 4b, the connected components detection results in a segmentation of the pixels in the following groups: outermost area 31, contours and possible undesirable inclusions 32, and two areas 33, 34, the latter of which being in the example a central lumen which does not belong to the ROI;

2) creating a "depth map" (FIG. 4c) which is an image with the same size as the destination slice. The "depth map" is a pixel data buffer which associates, for each pixel in the destination slice, an integer "depth" value that determines if the pixel is "inside", "outside", or "undefined". Initialize all pixels 35 previously identified as "outside" by the connected components detection to "out" value (0). The rest of the pixels 36 is set to "undefined" (−b 1) value. During the process iterations, the pixels of the depth map will be updated to reflect the localization ("in" or "out") of the pixels in the destination slice relative to the outermost area;

3) initializing a "current depth" parameter to "outside";

4) "Peeling process": as long as there are contour points in the contour image (FIG. 4d), repeating:

(i) finding "next" contour point 37 in the contour image to be filled. The "next" contour point is defined as the leftmost and topmost pixel in the contour image. Retrieve depth value associated with that pixel from depth map (this depth value being read from the previously initialized depth map);

(ii) extracting contour's exterior hull 38 (FIG. 4e) using a classical contour following algorithm. It eliminates any "inside" contour that would be located within the hull;

(iii) applying a connected components detection on hull (FIG. 4f). It generates 3 distinct areas: outside of the shape 39, contour of the shape 40, and interior of the shape 41;

(iv) using connected components image from previous step (FIG. 4f) to update the depth map (FIG. 4g) for the pixels 42 located inside the hull in 2D area 43. Hull contour pixels 40 are marked with current depth ("outside" on FIG. 4g), hull interior pixels 42 are marked as current depth's complementary ("inside" on FIG. 4g);

(v) subtracting hull's contour points 40 from contours image (FIG. 4a), which leads to FIG. 4h which becomes the new contours image, replacing FIG. 4d in the next iteration;

(vi) Setting current depth to its own complementary value (that is "inside" if it was "outside" and vice versa) for the next iteration, (vii) repeating the iteration at step (i).

5) finally, restoring the missing source outer contours in the depth map obtained after the iterations using connected components image (FIG. 4b). It is done to restore the original shape contours, which were lost during the peeling process in step 4 (hull contours 40 are set to the current pixel depth in FIG. 4f, which is "outside" in the first iteration). This step is thus simply setting the original contour pixel's depth to "inside" so they are not lost. FIG. 4i and FIG. 4j show the depth map before and after, respectively, restoring the original shape contours.

At the end of the process, the depth map (FIG. 4j) holds the status "inside" or "outside" for each and every pixel of the original image. The depth map is thus the correctly filled result image.

The pixels of the ROI are the "inside" pixels 44. In the example of FIG. 4, the ROI corresponds to a hollow structure with a lumen (such as a blood vessel).

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents and variations that are within the spirit and scope of this invention.

The invention claimed is:

1. A method for calculating a region of interest in a second image using an initial region of interest in a first image, the first and second images being linked by a spatial transformation function, the method comprising:
- generating a first polygonal mesh enclosing the initial region of interest in the first image;
- computing a second polygonal mesh in the second image by applying the spatial transformation function to said first polygonal mesh;
- identifying image elements within the second image that belong to an area enclosed by said second polygonal mesh;
- computing intersections of the second polygonal mesh with a 2D second image, so as to generate a 2D contour image;
- identifying image elements of said 2D second image that belong to at least one area enclosed by contours of the 2D contour image;
- applying a connected components detection to the 2D contour image so as to obtain a 2D image, where 2D areas located outside any closed shape are marked as outside;
- creating a depth map image in a form of a buffer associating to pixels of said 2D image one of the following depth values: complimentary values inside, or outside, or undefined;
- initializing in said depth map image the pixels previously identified as outside by the connected components detection to outside value; and
- filling said depth map image by iteratively identifying areas enclosed by contours from an outermost to an innermost contour, each contour separating outside pixels and inside pixels, said inside pixels defining 2D regions of interest.

2. The method of claim 1, wherein the spatial transformation function comprises soft deformations.

3. The method of claim 1, which further comprises the steps of:
- decomposing a 3D second image as a stack of 2D second images;
- computing 2D regions of interest in said 2D second images; and
- combining said 2D regions of interest to obtain a 3D region of interest.

4. The method of claim 1, which further comprises the steps of:
- generating an octree storing references to locations of the second polygonal mesh's faces, and
- computing intersections of said second polygonal mesh with said 2D second image using said octree.

5. The method of claim 1, wherein the spatial transformation function comprises only rigid body transformations and/or scaling.

6. The method of claim 5, which further comprises the steps of:
- identifying couples of first picture elements of said first polygonal mesh, that bound line segments included in said initial region of interest and oriented along at least one direction of said first image;
- computing the second polygonal mesh in the second image by applying the spatial transformation function to said couples of first picture elements, so as to compute corresponding couples of second picture elements; and
- computing picture elements of said second image, that belong to line segments bounded by said corresponding couples of second picture elements, using a rasterization algorithm and taking into account a segment thickness so as to avoid any space left between neighboring segments.

7. The method of claim 1, wherein spatial samplings for the first and second images are different.

8. The method of claim 1, wherein the first image is a reference image or an image from an anatomical atlas.

9. The method of claim 1, wherein the first and second images are acquired using distinct medical imaging techniques.

10. The method of claim 1, wherein the first and second images are acquired using at least one of the following medical imaging techniques: computed tomography (CT), magnetic resonance imaging (MRI), positron emission tomography (PET), and ultrasound imaging.

11. A method for calculating a region of interest in a second image using an initial region of interest in a first image, the first and second images being linked by a spatial transformation function, the method comprising:
- generating a first polygonal mesh enclosing the initial region of interest in the first image;
- computing a second polygonal mesh in the second image by applying the spatial transformation function to said first polygonal mesh;
- identifying image elements within the second image that belong to an area enclosed by said second polygonal mesh;
- computing intersections of the second polygonal mesh with a 2D second image, so as to generate a 2D contour image;
- identifying image elements of said 2D second image that belong to at least one area enclosed by contours of the 2D contour image;
- applying a connected components detection to the 2D contour image so as to obtain a 2D image, where 2D areas located outside any closed shape are marked as outside;
- creating a depth map image in a form of a buffer associating to pixels of said 2D image one of the following depth values: complimentary values inside, or outside, or undefined;
- initializing in said depth map image the pixels previously identified as outside by the connected components detection to outside value;
- filling said depth map image by iteratively identifying areas enclosed by contours from an outermost to an innermost contour, each contour separating outside pixels and inside pixels, said inside pixels defining 2D regions of interest;
- extracting an outermost contour's exterior hull in said 2D contour image using a contour following algorithm, said outermost contour being chosen from a criterion related to its vicinity with borders of said 2D contour image;
- applying connected components detection on said contour hull so as to generate distinct areas corresponding to, respectively: the outside of the contour, the contour and the interior of the contour;
- updating the depth map image by marking hull contour pixels with current depth value, and hull's interior area pixels with current depth's complementary value;
- removing said extracted contour from said 2D contour image; and
- setting the current depth value to its complementary value for the next iteration.

* * * * *